United States Patent
Fermann et al.

(10) Patent No.: US 9,097,656 B2
(45) Date of Patent: Aug. 4, 2015

(54) METHODS FOR PRECISION OPTICAL FREQUENCY SYNTHESIS AND MOLECULAR DETECTION

(71) Applicant: IMRA AMERICA, Inc., Ann Arbor, MI (US)

(72) Inventors: Martin E. Fermann, Dexter, MI (US); Marco Marangoni, Milan (IT); Davide Gatti, Ballabio (IT)

(73) Assignee: IMRA AMERICA, INC., Ann Arbor, MI (US)

( * ) Notice: Subject to any disclaimer, the term of this patent is extended or adjusted under 35 U.S.C. 154(b) by 256 days.

(21) Appl. No.: 13/851,521

(22) Filed: Mar. 27, 2013

(65) Prior Publication Data

US 2015/0185141 A1    Jul. 2, 2015

Related U.S. Application Data

(60) Provisional application No. 61/617,482, filed on Mar. 29, 2012.

(51) Int. Cl.
| | |
|---|---|
| *G01J 3/45* | (2006.01) |
| *H01S 3/13* | (2006.01) |
| *G01N 21/3504* | (2014.01) |
| *G01J 3/10* | (2006.01) |
| *G01N 33/00* | (2006.01) |
| *G02F 1/35* | (2006.01) |
| *H01S 5/0687* | (2006.01) |
| *H01S 3/00* | (2006.01) |

(52) U.S. Cl.
CPC ............. *G01N 21/3504* (2013.01); *G01J 3/108* (2013.01); *G01N 33/0027* (2013.01); *G02F 1/353* (2013.01); *G02F 1/3534* (2013.01); *H01S 3/0092* (2013.01); *H01S 5/0687* (2013.01); *G01N 2201/06113* (2013.01)

(58) Field of Classification Search
CPC ................ G01N 21/3504; G01N 2201/06113; G01N 33/0027; G02F 1/353; G02F 1/3534; G02B 6/02295; H01S 3/0092; H01S 5/0092; H01S 5/0687
See application file for complete search history.

(56) References Cited

U.S. PATENT DOCUMENTS

| | | | |
|---|---|---|---|
| 4,590,597 A | 5/1986 | Long-Sheng et al. | |
| 5,903,358 A * | 5/1999 | Zare et al. ...................... | 356/437 |
| 6,633,596 B1 | 10/2003 | Wulfmeyer et al. | |
| 6,727,492 B1 * | 4/2004 | Ye et al. ................... | 250/227.18 |
| 6,891,149 B1 | 5/2005 | Lewis et al. | |
| 7,809,222 B2 | 10/2010 | Hartl et al. | |
| 2003/0189711 A1 * | 10/2003 | Orr et al. ....................... | 356/484 |

(Continued)

OTHER PUBLICATIONS

A. Cingöz et al., 'Direct Frequency Comb Spectroscopy in the Extreme Ultraviolet', Nature, 482, 68 (Feb. 2, 2012).

(Continued)

*Primary Examiner* — Michael A Lyons
(74) *Attorney, Agent, or Firm* — Sughrue Mion, PLLC; Richard C. Turner

(57) ABSTRACT

The present invention relates to precision linewidth control and frequency measurements of continuous wave lasers for the near to far IR spectral regions, precision frequency synthesizers and exemplary applications in molecular detection. Methods and systems are disclosed for simultaneous line narrowing of cw lasers, as well as referencing the desired emission wavelength to a frequency comb laser.

14 Claims, 8 Drawing Sheets

(56) References Cited

U.S. PATENT DOCUMENTS

| | | | |
|---|---|---|---|
| 2004/0017833 | A1 | 1/2004 | Cundiff et al. |
| 2004/0136413 | A1* | 7/2004 | Kallmann et al. ............. 372/20 |
| 2007/0272838 | A1* | 11/2007 | Kudo et al. ............. 250/227.12 |
| 2010/0225897 | A1 | 9/2010 | Fermann et al. |
| 2012/0205352 | A1 | 8/2012 | Fermann |
| 2012/0236314 | A1 | 9/2012 | Fermann |
| 2013/0293946 | A1* | 11/2013 | Fermann et al. ............. 359/330 |

OTHER PUBLICATIONS

A. Cygan et al., "Pound-Drever-Hall-locked (PDH), frequency-stabilized cavity ring-down spectrometer", Rev. Scientific Instr., vol. 82, pp. 063107 (Jun. 16, 2011).

E. A. Donley et al., "Double-pass acousto-optic modulator system", Rev. of Scientific Instruments, vol. 76, pp. 063112 (Jun. 1, 2005).

R.W.P. Dreyer et al., "Laser Phase and Frequency Stabilization", Appl. Phys. B, vol. 31, pp. 97-105 (Feb. 10, 1983).

I. Galli et al., "Molecular Gas Sensing Below Parts per Trillion: Radiocarbon-Dioxide Optical Detection", Phys. Rev. Lett., vol. 107, pp. 270802 (Dec. 30, 2011).

D.J. Hamilton et al., "A quantum cascade laser-based optical feedback cavity-enhanced absorption spectrometer for the simultaneous measurement of CH4 and N2O in air", Appl. Phys. B, vol. 102, pp. 879-890 (Oct. 17, 2010).

Fig. 10.4 of "Building Electro-Optical Systems" by P. C. D. Hobbs, John Wiley & Sons (© 2000) p. 332.

K. Knabe et al., "Frequency Characterization of an External-Cavity Quantum Cascade Laser at 4.5 µm using a Frequency Comb," in Lasers, Sources, and Related Photonic Devices, OSA Technical Digest, ASSP paper LT1B.4 Jan. 2012. also Optics Express 20, (11) 12432-12442 (Jan. 9, 2012).

R. Z. Martinez et al., "Laser-locked, high-repetition-rate cavity ringdown spectrometer", J. Opt. Soc Am. B, vol. 23, pp. 727 (Apr. 4, 2006).

T.R. Schibli et al., "Phase-locked widely tunable optical single-frequency generator based on a femtosecond comb", Opt. Lett., vol. 30, pp. 2323-2325 (Sep. 1, 2005).

\* cited by examiner

METHODS FOR PRECISION OPTICAL FREQUENCY SYNTHESIS AND MOLECULAR DETECTION

FIELD OF THE INVENTION

The present invention relates to precision linewidth control and frequency measurements of continuous wave lasers for the near to far IR spectral regions, precision frequency synthesizers and exemplary applications in molecular detection.

BACKGROUND

Tunable continuous wave (cw) lasers are essential tools for precision spectroscopy applications such as trace gas detection and frequency measurements. Trace gas detection is particularly sensitive when coupling the cw lasers into a high finesse gas-filled external enhancement cavity which greatly increases the interaction length of the trace gases with the cw light. Because many commercially available cw laser sources, particularly quantum cascade lasers, have relatively large emission linewidths, they cannot be efficiently coupled into high finesse enhancement cavities, which can have acceptance bandwidths as low as 10 kHz, or even lower.

Generally this requirement is resolved by electronic or optical locking techniques. In electronic locking, active feedback components that electronically control the emission wavelength of the cw laser (R. W. P. Dreyer et al., Laser Phase and Frequency Stabilization, Appl. Phys. B, vol. 31, pp. 97-105 (1983)) are provided. Alternatively, electronic locking can also be accomplished by appropriately applying a frequency modulation to the emission wavelength of the cw laser to match the cw laser emission frequency to a resonance frequency of an enhancement cavity (R. Z. Martinez et al., Laser-locked, high-repetition-rate cavity ring-down spectrometer, J. Opt. Soc. Am. B, vol. 23, pp. 727 (2006)).

Optical locking generally uses self-injection of cw laser light as filtered by an external cavity to automatically lock the laser light to the cavity (D. J. Hamilton et al., "A quantum cascade laser-based optical feedback cavity-enhanced absorption spectrometer for the simultaneous measurement of $CH_4$ and $N_2O$ in air", Appl. Phys. B, vol. 102, pp. 879-890 (2011)). With an optical locking laser, linewidths less than the cavity line width can be obtained.

A well-established method for trace gas detection is cavity ring down spectroscopy, which can be conveniently combined with optical locking techniques as described by Hamilton as well as electronic locking techniques as described by Martinez et al. An extensive review of cavity ring down spectroscopy methods was recently published by A. Cygan et al., Pound-Drever-Hall-locked (PDH), frequency-stabilized cavity ring-down spectrometer, Rev. Scientific Instr., vol. 82, pp. 063107 (2011).

SUMMARY OF THE INVENTION

An aspect of the present invention features methods and systems for simultaneous line narrowing of cw lasers, as well as referencing the desired emission wavelength to a frequency comb laser. The beat frequency between an individual comb tooth from the frequency comb laser and the emission frequency of a cw laser is detected with and derived from a detector which receives a filtered output from the comb laser. The signal is fed forward to an acousto-optic frequency shifter (AOFS) downstream from the cw laser to produce a cw laser output which is frequency shifted and locked to the individual comb tooth. Such an arrangement allows for rapid corrections of the emission frequency of the cw laser without the use of a high bandwidth electronic feedback loop. Any slow drifts of the cw laser frequency can further be compensated by a feedback loop that coarsely stabilizes this beat frequency. Additional arbitrary frequency offsets between the cw laser output frequency and the frequency of the comb tooth can also be incorporated by a local oscillator operating at an offset frequency.

Rapid modulation of the frequency of the cw laser can be incorporated by modulation of the frequency of the local oscillator, the mean drive frequency of the AOFS or the frequency of the individual comb tooth.

Widely tunable cw laser light with precisely known frequencies can be further obtained by locking the cw laser to different individual comb lines or by tuning the location of an individual comb line by, for example, scanning the repetition rate of the frequency comb laser.

The cw laser can be used in conjunction with an external enhancement cavity for trace gas detection via cavity ring down spectroscopy, where the cw laser can be efficiently coupled into the cavity while slowly scanning the cavity length. The frequency comb then provides a simultaneous measurement of the laser frequency.

Cavity ring down signals at high repetition rates can further be obtained by, prior to a detection stage, electronically locking a line narrowed cw laser to a cavity resonance of the external ring down cavity for improved trace gas detection sensitivity. Any cw laser light can be used in this scheme, but of particular interest are quantum cascade lasers as well as widely tunable quantum cascade lasers that have typically broad emission line widths and where line narrowing is typically very difficult to perform.

In the mid-IR spectral region from 3-13 μm, Ge based AOFSs can be implemented. Suitable alternatives include GaAs or GaP based AOFS.

To determine the exact frequency of the cw laser output, precision interferometers, generally known as wavemeters, can be implemented to coarsely measure the cw laser frequency, for example to within 30-50% of the spacing of individual comb lines of the frequency comb laser. Measurements of the carrier envelope offset frequency of the comb laser and the repetition rate of the comb can then be used to determine the precise frequency of the cw laser.

The exact frequency of the cw laser can also be obtained from a measurement of the repetition rate of the comb laser and the carrier envelope offset frequency at two or more different repetition rates while locking the cw laser to different comb lines. These frequency measurements do not require the use of any external optical frequency references or wavemeters. However, the repetition rate of the comb lines is preferably phase-locked to an external RF frequency reference, such as a GPS signal. To avoid ambiguities, comb lasers with large repetition rates are preferred. For example the comb repetition rates can be larger than 250 MHz.

For the determination of the emission frequency of cw lasers emitting in the mid-IR spectral region, it is further advantageous to implement optical up-conversion to transfer any beat frequency measurements to the near IR, where detectors with GHz optical bandwidths are available. For example, sum frequency generation can be implemented between the cw laser and the frequency comb lasers to generate a frequency up-converted comb structure. The frequency comb lasers can then be further coupled into a super continuum fiber, allowing for the measurement of the beat signal between the super continuum and the frequency up converted comb laser, from which the frequency of the cw laser can be determined. To obtain a good signal/noise ratio for the beat signal, the implementation of frequency comb lasers with high repetition rates, preferably higher than 250 MHz are desirable.

The determination of the emission frequency of cw lasers via upconversion is particularly useful with widely tunable lasers, such as optical parametric oscillators, widely tunable fiber or solid state lasers and diode or quantum cascade lasers.

Frequency up-conversion of a comb laser for frequency measurements of a cw laser can further be combined with line narrowing using an AOFS to obtain a broadly tunable narrow linewidth optical frequency synthesizer. The advantage of frequency up-conversion in this application is that no control of the carrier envelope offset frequency of the comb laser is required. For improved linewidth of the frequency synthesizer output, phase locking of at least one comb tooth of the frequency comb laser to at least one external narrow linewidth reference laser is beneficial. Such schemes can be used in a feed forward configuration, where an error signal is obtained without the cw light passing the AOFS. Alternatively, a feedback configuration is also possible, where an error signal is obtained after the cw light passes through the AOFS. Feedback configurations are beneficial for ultimate long term precision. For improved control bandwidth of the frequency synthesizer the AOFS can be combined with an electro-optical modulator (EOM), both in feed-forward and feed-back configuration.

To obtain high signal/noise ratios of the error signals in up-conversion frequency synthesizers it is useful to implement an additional AOFS to obtain a frequency shifted replica of the frequency comb.

Optical frequency synthesizers are useful for any type of spectroscopy and can for example also be combined with cavity ring down spectroscopy as well as photo-acoustic detection of trace gases.

DETAILED DESCRIPTION

Figure 1:
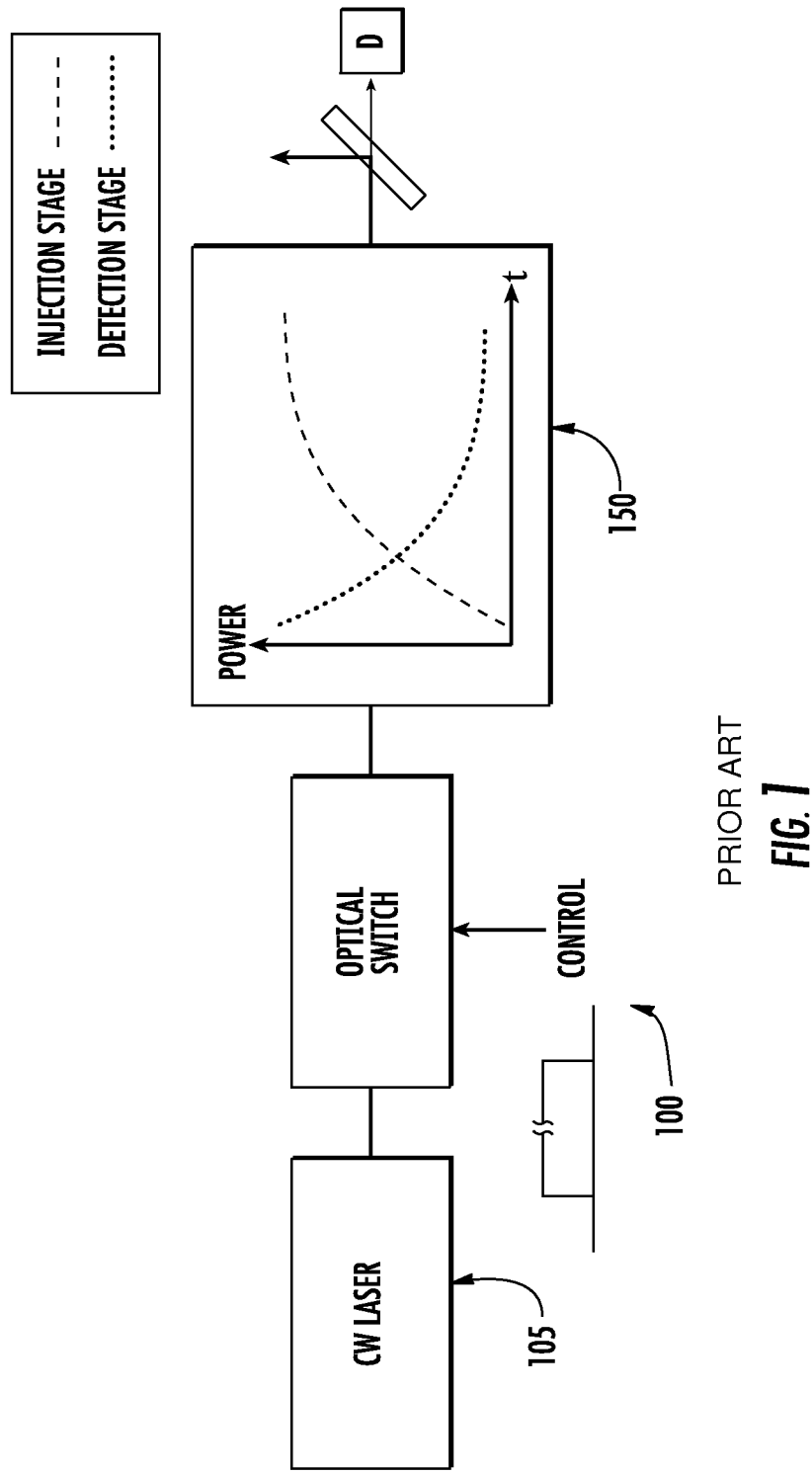
FIG. 1 schematically illustrates a conventional configuration for cavity ring down spectroscopy.

A conventional cavity ring down spectrometer configuration 100 is further depicted in FIG. 1. Generally, a cw laser output is injected into the ring down cavity, leading to a buildup of the optical power, referred to herein as intra-cavity signal evolution within the ring down cavity. FIG. 1 schematically illustrates such an arrangement having cw laser 105 and ring down cavity 150, with an optical switch disposed therebetween. In at least one embodiment the optical switch controls transmission. The optical switch may include an acousto-optic or electro-optic device in either bulk or integrated form. Cw laser injection can be controllably interrupted with the optical switch. When the optical switch is controlled to allow transmission (e.g.: closed with a TTL control signal), the cw beam is injected into the ring cavity, with intra-cavity signal evolution illustrated with the buildup of power in ring-down cavity 150. When the switch prevents transmission, the diminishing intra-cavity optical power is monitored with detector D receiving light leaking from a cavity mirror. In the present disclosure we refer to the time period during which cw light is injected into the cavity as the light injection stage and the time period during which cw light leaking from the cavity is detected as the detection stage. As is well known in the state of the art, for high finesse cavities the light leaks from a ring-down cavity within 1 μs-1 ms. The detector thus measures a decaying signal during the detection stage, nominally of exponential form, which is sometimes referred to as the ring down signal or ring down trace.

Cavity ring-down detection techniques generally benefit from a maximization of the acquisition rate at which ring down traces can be acquired. For example, this can be done by using electronic locking of the ring down cavity to a cw laser during the injection stage as discussed by Martinez et al. Optical locking during the injection stage is another method for maximization of the acquisition rate. However, a complication arises because during the detection stage, the optical or electronic lock to the cavity is lost. The cavity lock has to be reestablished prior to the injection stage. As a result, a significant time lag can occur between the injection and the detection stage, thus leading to an undesirable increase in the acquisition rate of ring down signals. Also additional frequency noise can be added to the cw laser leading to a variation in cavity ring-down times.

Rather than locking the cw laser to the cavity, a broadband cw laser can be used during the injection stage, where the optical cavity filters the appropriate optical cw laser frequency bandwidth that matches the cavity linewidth. However, this minimizes the injection efficiency of the cw laser light into the cavity.

Alternatively, a narrowband cw laser cavity can be used for injection without the implementation of any cavity locking techniques. However, a relatively slow cavity scan needs to be implemented between the injection and detection stages, which minimizes the possible acquisition rate for ring-down signals.

Moreover, none of these cavity ring down spectroscopy methods provide an absolute measurement of the cw laser frequency. A precision interferometer, generally known as a wavemeter, or optical reference absorption cells are further needed to determine the frequency of the cw laser light. In addition, the methods allow for only limited and relatively slow wavelength tunability. However, multi-species trace gas detection requires relatively large wavelength tuning ranges that can be as large as 100 cm$^{-1}$, 1000 cm$^{-1}$ or even larger. Moreover, broad wavelength tuning is highly desirable for detection of different trace gases. Equally, cavity ring-down spectroscopy with quantum cascade lasers (operating in the technologically important molecular fingerprint region) and electronic locking techniques have not been demonstrated so far.

Cavity ring down spectroscopy, as well as other spectroscopy techniques, benefit greatly from the availability of optical frequency synthesizers, where we define optical frequency synthesizer as a cw source with freely selectable optical frequency within a certain tuning range and calibrated emission frequency. For example when using cavity ring down spectroscopy, optical synthesizers allow the probing of molecular absorption lines at different cavity modes. In conjunction with photo-acoustic detection, frequency synthesizers allow a straight forward identification of actual absorption lines and measurement of their frequency. In the prior art, cw laser frequency synthesis has been performed using, for example, frequency counters in conjunction with a frequency comb laser and a frequency shifted frequency comb replica, as discussed by T. R. Schibli et al., 'Phase-locked widely tunable optical single-frequency generator based on a femtosecond comb', Opt. Lett, vol. 30, pp. 2323-2325 (2005). However, no methods have yet been described that combine frequency synthesis with frequency up-conversion.

Figure 2:
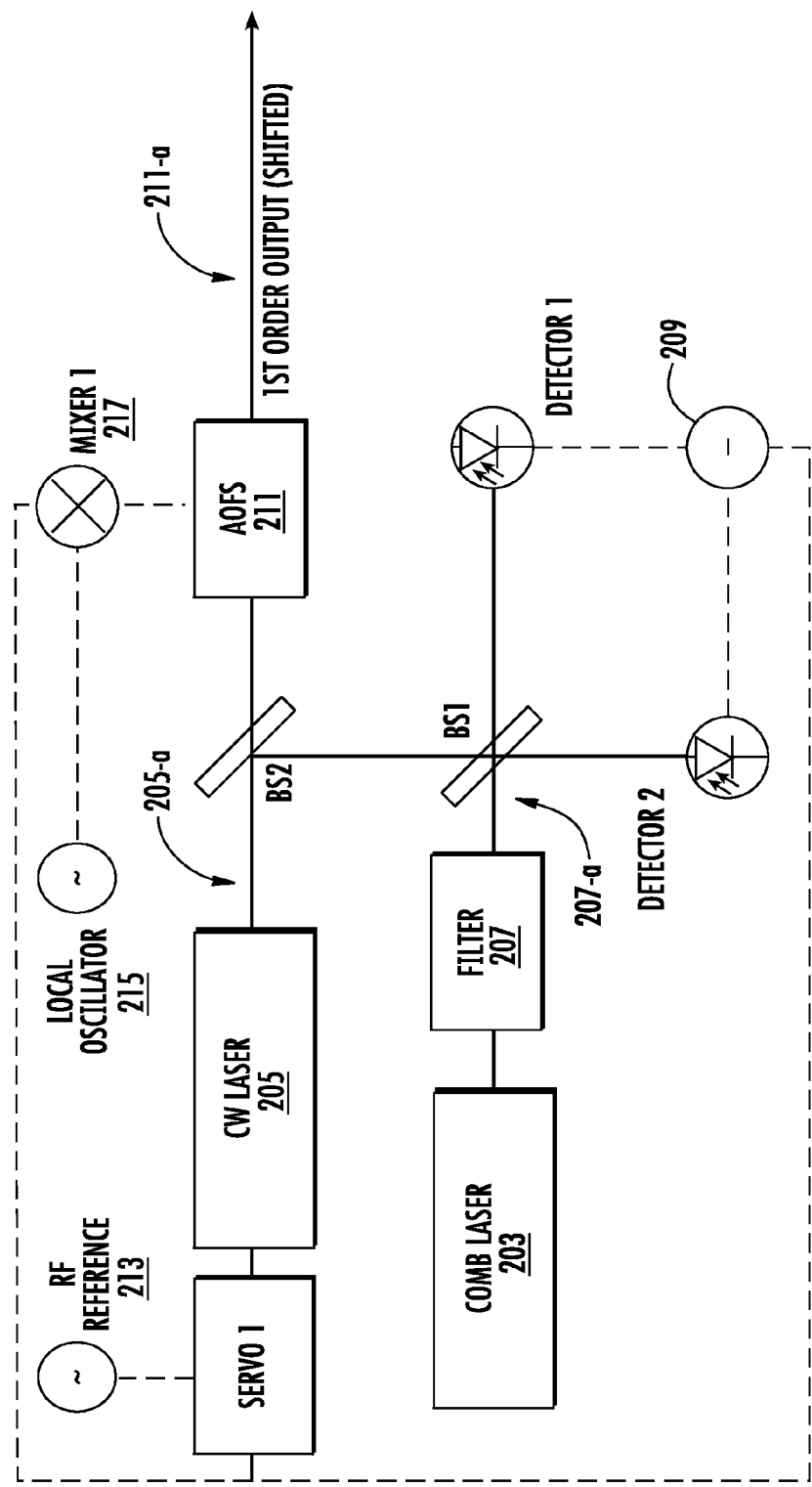
FIG. 2 schematically illustrates an exemplary embodiment for line narrowing of cw lasers with a comb laser and an acousto-optic modulator in a feed-forward configuration.

An exemplary embodiment of line narrowing of a cw laser with an AOFS is shown in FIG. 2. The path of optical signals in line narrowing system 200 is shown in solid lines, and the path of electronic signals is shown as dashed lines. The cw laser 205 can be any tunable laser source emitting continuous wave radiation, for example external cavity diode lasers (ECLs) or preferably any form of quantum cascade laser (QCL). The frequency comb laser 203 can be a fiber comb laser, but any other suitable frequency comb system based on solid-state lasers, diode lasers or micro-resonators as known in the state of the art can also be implemented. The comb laser 203 generates a frequency comb that is filtered to limit the number of comb lines at the output of filter 207. As shown in FIG. 2, a portion of the output from the cw laser 205 is delivered with beam splitter BS2, or a suitable combination of beam splitting/combining optics, to an acousto-optic frequency shifter which will be discussed below. The filtered output 207-a of comb laser 203 is optically combined with a portion of the output 205-a of cw laser 205 via beam splitter BS1, and the beat signal between the cw laser output and one of the individual comb teeth from the frequency comb laser is derived from signals obtained with a detection system which includes detectors 1 and 2 and downstream RF filters (not shown). Since the output from the cw laser 205 and the filtered comb laser signal 207-a are combined at beam splitter BS1, dual balanced detection between the two detectors can further be implemented to maximize the signal/noise ratio of the beat signal. The dual balanced detector 209 is depicted here with a minus sign surrounded by a circle.

In addition to the shown dual balanced detectors, also optical single side-band (SSB) mixers using optical hybrids can be employed for beat frequency detection. Optical SSB mixers are well known in the state of the art and are, for example, shown in FIG. 10.4 of 'Building Electro-Optical Systems' by P. C. D. Hobbs, John Wiley & Sons (2000) and are not further described here. The incorporation of SSB mixers in FIG. 1 requires the substitution of the two detectors in FIG. 1 with two pairs of balanced detectors for in-phase detection and quadrature detection of the respective beat signals, thus allowing the direct measurement of the phase evolution of the optical signals. Optical hybrids have the advantage that the ambiguity of the sign of the beat signal is removed, and thus it can be determined which frequency is higher. In other words, the optical hybrid can be configured to produce only one beat signal within the frequency span determined by the comb spacing of the comb laser. Moreover, phase information is also obtained when the frequency of the cw laser and the frequency of an individual comb line are identical or nearly identical; the frequency evolution can then be determined by taking the time derivative of the phase evolution.

The beat signal at the output of dual balanced detector 209 is selectively filtered (not shown) with radio-frequency (RF) filters to isolate a single beat frequency corresponding to an individual comb line. The beat frequency is then stabilized to a preset value $\Delta f_0$ in conjunction with a stabilizer (not separately shown) which includes feedback loops for laser system stabilization, including a slow electronic servo loop, servo 1, to coarsely stabilize the emission frequency of the cw laser. This can, for example, be accomplished by generating an error signal between the beat signal and the depicted external RF frequency reference 213 at the frequency $\Delta f_0$ via a phase detector incorporated within servo 1, and further using the servo 1 to control the drive current when using a cw diode laser, or to control a piezo-electric transducer when using an external cavity diode laser. In some embodiments a combination of a cw diode and an external cavity diode laser may be utilized. As an alternative to implementing a phase-detector-servo loop for slow feedback control, a frequency counter can be used, which is referenced to an external frequency standard via a feedback loop. Preferably the counter and stabilizer feedback loops are conveniently implemented digitally in a field-programmable gate array (FPGA), microcontroller or digital signal processing (DSP) configuration, as for example demonstrated by Schibli et al.

In an exemplary embodiment, the beatnote signal between the cw laser 205 and an individual mode of the frequency comb can be recorded by a 125 MHz-bandwidth photodetector(s). The phase detector inside servo 1 (not shown) is further employed to compare the phase of the beatnote selected to be nominally at a frequency of 10 MHz with that of a 10 MHz RF reference signal. The RF reference signal 213 is provided by a signal generator referenced to a RF frequency standard such as a GPS signal, and the difference signal, after being processed by servo 1, is fed back to modulate the frequency of the cw laser 205. In this way the cw laser is forced to oscillate at a frequency which is, for example, frequency shifted by 10 MHz with respect to the selected individual mode (line) of the frequency comb. The servo control can be implemented by digital or analog electronics.

In an exemplary embodiment digital servo control is used and the control of servo 1 can be derived from an FPGA-based proportional-integral-derivative (PID) controller, as well known in the state of the art, with a bandwidth of 1 MHz, and fully controllable by a personal computer as available from Toptica Photonics AG, with Model Digilock 110. The signal from the phase detector is further suitably amplified in order to match the dynamic range of the high speed analogue to digital converter ADC (±2V, 14 bits, 100 MS/s) at the servo input. The digitized signal can then be compared with a predetermined value set by the user to generate the error signal and, after PID amplification, can be back converted to analogue by a digital to analogue converter DAC (±6.5 V, 16 bits, 100 kS/s) and sent to a frequency modulation port of the cw laser 205, which may conveniently be a diode laser, to modulate its optical frequency. The loop bandwidth is ultimately limited by the typical limited bandwidth of such a modulation port, which in this exemplary implementation was 2 kHz. However, higher modulation bandwidths, up to the GHz range, are also possible.

Referring back to FIG. 2, the beat signal is further mixed with a local oscillator RF source 215 to produce a mean excitation frequency, $\bar{f}_{aofs}$, for the AOFS. The mixer 217 is denoted with the cross within a circle. $\bar{f}_{aofs}$ is preferably selected to enable efficient excitation of acoustic waves within the AOFS and to produce a high diffraction efficiency. For example, the local oscillator frequency can be $f_{LO}=90$ MHz. By mixing $f_{LO}$ with $\Delta f_0$ an exemplary mean excitation frequency $\bar{f}_{aofs}=80$ MHz can be generated. The mean excitation frequency is further amplified by a low noise RF amplifier and allows for diffraction and frequency shifting of the cw laser by the AOFS. In various embodiments the first order diffracted signal is used.

The diffracted beam from the AOFS 211 then contains a line narrowed cw signal 211-a from the cw laser 205. This can be seen as follows. The diffracted beam contains the frequency shifted cw laser light, i.e.

$$f_{diff}=f_{cw}+\delta f_{cw}+f_{aofs}(t), \quad (1)$$

where $f_{diff}$ is the frequency of the cw light diffracted by the AOFS, $f_{cw}$ is the average emission frequency of the cw laser and $\delta f_{cw}$ contains any high frequency noise. $f_{aofs}(t)$ is derived from the mixing product of the local oscillator frequency $f_{LO}$ and the beat frequency $\Delta f_0$, i.e. $f_{aofs}(t)=f_{LO}-\Delta f_0$. $\Delta f_0$ is given by $\Delta f_0=f_{cw}+\delta f_{cw}-\nu_n$, where $\nu_n$ is frequency of the comb line nearest to the average emission frequency of the cw laser. As is well known $\nu_n$ is governed by the comb equation, $\nu_n=n\times \nu_{rep}+\nu_0$, where n is an integer, $\nu_{rep}$ is the repetition rate of the comb laser and $\nu_0$ is the carrier envelope offset frequency. Inserting the appropriate expressions into eq. (1), we obtain $$f_{diff}=f_{cw}+\delta f_{cw}+f_{aofs}(t)=f_{cw}\delta f_{cw}+f_{LO}-f_{cw}-\delta f_{cw}+\nu_n=f_{LO}+\nu_n.$$

It follows that the frequency of the diffracted light is given precisely by the optical frequency of one comb line $\nu_n$ plus the local oscillator frequency. In other words, the coherence of the comb line is transferred to the cw laser. The linewidth of the diffracted cw light is moreover determined by the linewidth of the individual comb tooth that the cw laser was locked to. To obtain a narrow linewidth, a narrow line width comb laser 203 is preferred. In a preferred embodiment, to ensure long term frequency stability of the line-narrowed cw light, stabilization of both the repetition rate and carrier envelope offset frequency of the frequency comb laser is implemented. Line width narrowing of the cw laser to a line width of 10 kHz or less is then possible, which in turn allows efficient coupling of the line narrowed light to a high finesse external enhancement cavity.

To tune or modulate the emission frequency of the line narrowed signal, either of $f_{LO}$, $\Delta f_0$ or $\nu_n$ can be tuned or modulated, provided that $f_{LO}-\Delta f_0$ falls within the modulation bandwidth of the AOFS. For example, $\nu_n$ can be tuned by changing the cavity length of the frequency comb laser as is well known in the state of the art. The response time of the line narrowed signal or the control bandwidth of the system is then limited by the propagation time of the acousto-optic wave in the AOFS. With commercially available AOFS units, control bandwidths of the order of 1 MHz are possible in the near IR and mid IR spectral region. Larger bandwidths are readily obtainable by combining an acousto-optic device with an electro-optic device. When using an electro-optic modulator, the diffracted and zero-order beam all propagate in the same direction, which means that only a fraction of the generated light becomes line-narrowed. A configuration using such an additional electro-optic modulator is not separately shown here.

In the near IR spectral region many different materials can be implemented for AOFS 211. For example, fused silica based AOFS can be implemented in the spectral range from 1-2 μm. Most currently commercially available AOFS units in the mid spectral range from 2.5-12 μm are germania based and allow for frequency shifts of the order of 80 MHz with a modulation bandwidth of 10-20 MHz. Much higher modulation bandwidths (of the order of a few 100 MHz-1 GHz) are possible using AOFS units based on $TeO_2$, GaAs and GaP. One drawback of using GaAs or GaP AOFS units is limited diffraction efficiency. However, because QCLs typically have high output powers, even diffraction efficiencies as low 10%, or possibly even lower, are acceptable. Line narrowing of QCLs with emission bandwidth of tens of MHz is possible, provided the variation of the actual laser emission frequency is sufficiently slow. Such slowly varying emission frequencies are typically encountered with broadly tunable external cavity QCLs. As for example shown by K. Knabe, P. A. Williams, F. R. Giorgetta, C. M. Armacost, M. B. Radunsky, and N. R. Newbury, "Frequency Characterization of an External-Cavity Quantum Cascade Laser at 4.5 μm using a Frequency Comb," in *Lasers, Sources, and Related Photonic Devices*, OSA Technical Digest (CD) (Optical Society of America, 2012), paper LT1B.4, the frequency noise spectral density of a typical QCL laser falls off with 1/f, e.g. the major contributions to line-broadening occur at low modulation frequencies.

The absolute emission frequency of the cw laser can be determined with the help of a wavemeter (not shown); where large comb spacing is beneficial to limit the complexity of the calibration routines of the wavemeter. Comb spacings of the order of 100 MHz are preferred, comb spacings of 300 MHz are even more desirable, and comb spacings of more than 1 GHz are most desirable. Once the frequency of the cw laser has been approximately determined by the wavemeter, knowledge of the repetition rate and carrier envelope offset frequency of the comb laser 203 can be used to precisely determine the frequency of the cw laser 205.

In various embodiments, the exact frequency of the cw laser 205 can, for example, be also obtained with an internal calibration routine without the use of a wavemeter. In this implementation, the beat frequency of the cw laser is measured with a first comb line of order n of the frequency comb laser. With the feedback to the cw laser off, the repetition rate of the comb laser is then changed to have a comb line of order m overlap with the emission frequency of the cw laser. Provided $\Delta n=n-m$ is known, the exact value of n or m can then be determined. Since $\Delta n$ can be tracked while changing the repetition rate of the comb laser, such a calibration routine can easily be incorporated. In order to avoid any ambiguity, it is further beneficial to repeat this procedure for more than two comb laser repetition frequencies. The exact details of such a calibration routine were for example recently described in A. Cingöz et al., 'Direct Frequency Comb Spectroscopy in the Extreme Ultraviolet', Nature, 482, 68 (2012) and are not further discussed here.

For some applications the frequency dependent beam pointing from the AOFS may be a limitation. However, as is well known in the state of the art, this can be eliminated by double passing the AOFS as described, for example, in E. A. Donley et al., 'Double-pass acousto-optic modulator system', Rev. of Scientific Instruments, vol. 76, pp. 063112 (2005). As is well known in the state of the art, a double-pass through an AOFS effectively doubles the modulation frequency, therefore the AOFS drive frequency needs to be divided by two to produce the right frequency correction to the cw laser.

Figure 3:
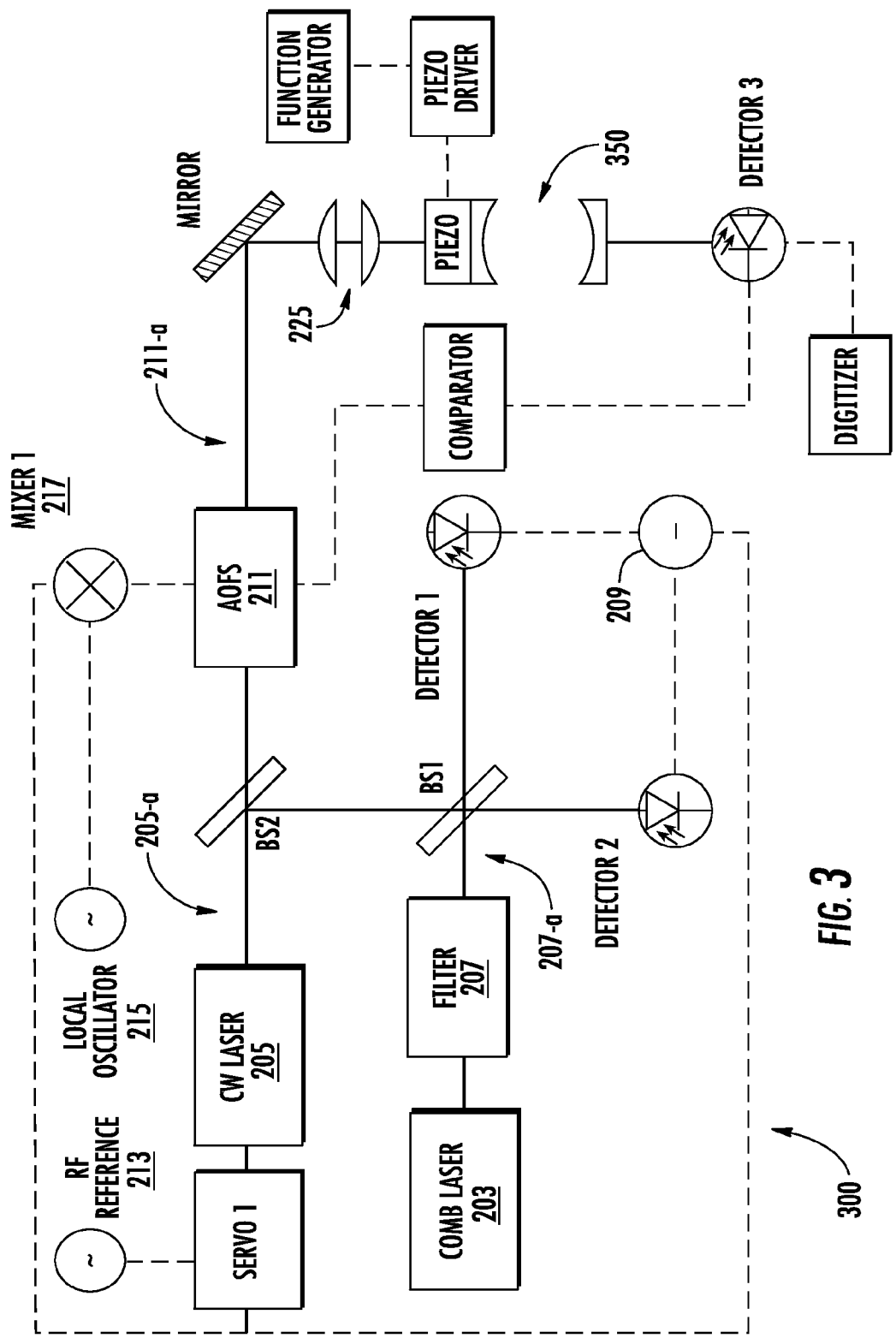
FIG. 3 schematically illustrates an exemplary embodiment for coupling a line narrowed cw laser to an external enhancement cavity for cavity ring down spectroscopy.

Laser line narrowing as described herein can be conveniently combined with cavity ring down spectroscopy for trace gas detection in system 300, shown in FIG. 3. As illustrated in FIG. 3, components similar or identical to those of FIG. 2 may be utilized to line narrow the cw laser output. Additionally, after being diffracted by the AOFS, the frequency shifted output 211-a derived from the line narrowed cw laser is coupled into a ring-down cavity 350 using an appropriate lens configuration (or telescope) 225 as shown in FIG. 3 for mode-matching. However, any other suitable bulk, integrated, and/or fiber optical components can also be used for mode-matching. The piezoelectric transducer is connected to a function generator which applies a ramp voltage to change the cavity length and is designed to sweep over at least one free spectral range of the ring-down cavity 350. The output light is focused onto detector 3, the output of which is sent to a digitizer to perform data analysis, as well as to a comparator operatively connected to the AOFS 211. The comparator turns the AOFS off when a predetermined signal level on the detector is obtained, thus terminating the injection stage. When the AOFS is turned off, the detection stage begins, and as discussed above with respect to FIG. 1, the light is no longer injected into the cavity and the intra-cavity light begins decaying with a decay rate proportional to any absorbing species in the cavity. The light leaking from the cavity during the detection stage, i.e. the ring-down signal, is detected or sampled with detector 3. The detected signal can further be digitized and sent to a computer for signal analysis.

The AOFS 211 advantageously performs two functions simultaneously, i.e. it is used for line-narrowing as well as for turning the ring down cavity 350 on and off. The comb laser 203 further provides for an absolute measurement of the laser frequency injected into the ring-down cavity 350. Thus, by using the AOFS 211 for line-narrowing, the cw laser 205 can be efficiently coupled into the cavity allowing for intra-cavity saturation of many molecular absorption lines. As recently shown by I. Galli et al., (in Molecular Gas Sensing Below Parts per Trillion: Radiocarbon-Dioxide Optical Detection, Phys. Rev. Lett., vol. 107, pp. 270802 (2011)), the saturation of molecular absorption lines in cavity ring down spectroscopy applications can indeed be used to maximize the sensitivity of trace gas detection.

Figure 3A:
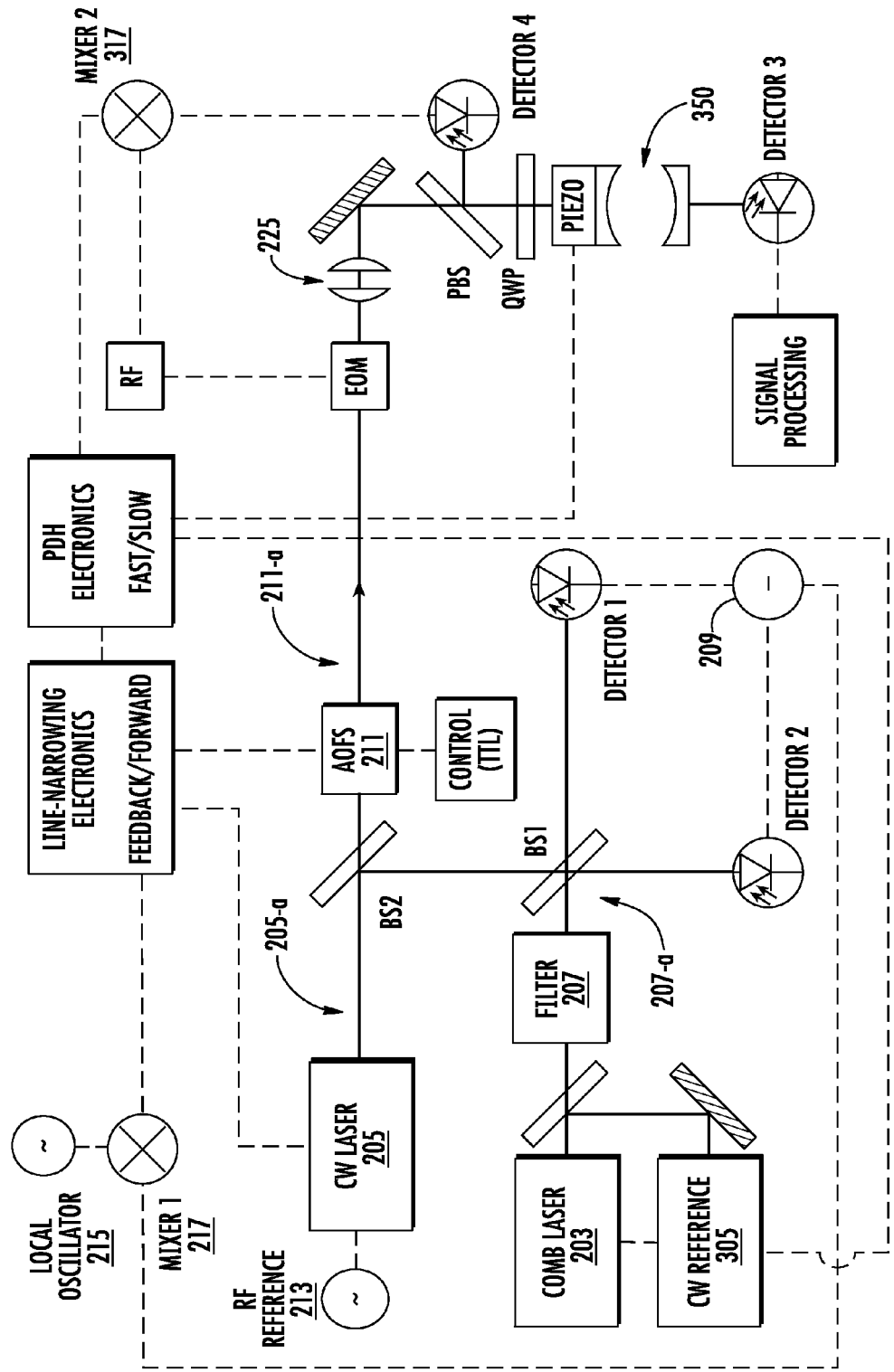
FIG. 3a schematically illustrates an alternative embodiment for coupling a line narrowed cw laser to an external enhancement cavity for cavity ring down spectroscopy.

A disadvantage with the system shown in FIG. 3 is the need for cavity length sweeping, which can take an extended amount of time and thus reduces the possible acquisition rate of ring down signals. The time intervals needed between the acquisition of individual ring down traces can be greatly reduced by the implementation of a locking technique which locks the line narrowed laser to one of the cavity resonances. This can be conveniently done with the implementation of a Pound Drever Hall locking (PDH) scheme as schematically illustrated in FIG. 3a.

Previously, a Pound Drever Hall locking scheme was applied to an AOFS line narrowed Ti; sapphire laser to maximize the acquisition rate of cavity ring down signals as described in R. Z. Martinez et al., 'Laser-locked, high-repetition-rate cavity ring-down spectrometer', J. Opt. Soc Am. B, vol. 23, pp. 727 (2006). However, a limitation with the Martinez approach is that the line narrowing AOFS is turned off during the ring-down detection stage and no error signal for line narrowing is detected.

With the implementation of a feed forward scheme for line-narrowing, the error signal for line narrowing and frequency control of the cw laser is continuously recorded even when the AOFS is turned off during acquisition of a ring down signal. Hence the cw laser can be rapidly locked to a cavity resonance when the AOFS is turned back on during the signal build-up stage, provided the ring down cavity resonances drifts only minimally when the AOFS is turned off.

This operation is further described with reference to FIG. 3a. Several components upstream of the AOFS are essentially identical to the ones described with respect to FIG. 2. Note the servo between RF reference 213 and cw laser 205 is not separately shown. However, we include here an additional cw reference laser 305 to which one of the comb lines from the comb laser is locked. Locking of comb lasers to cw lasers is well known and not further described here. A PDH locking scheme is implemented to lock the cw laser to a cavity resonance when the AOFS is turned on. The PDH locking scheme includes an additional electro-optic modulator (EOM) downstream from the AOFS 211, which imparts frequency modulation sidebands onto the cw laser frequency, which are simultaneously line narrowed by the AOFS. In various embodiments, the EOM is modulated at frequencies between 1-100 MHz with the shown RF source. The light reflected from the cavity is detected by detector 4 and mixed with an RF source signal in mixer 2 (317) to produce an error signal which is then amplified (not shown) and sent to the PDH control electronics which generates signals for frequency correction that are applied to various elements of the system. In some embodiments, up to three transducers with various frequency responses are implemented to maintain a tight lock between the cw laser 205 frequency and a cavity resonance. For example the ring-down cavity length, the AOFS modulation frequency, and/or the comb laser repetition rate can be controlled by the PDH control electronics.

For control of the ring down cavity length, a control signal from the PDH control electronics is directly applied to a piezo-electric transducer as shown in FIG. 3a. To control the repetition rate of the comb laser 203, the PDH control signal can be directed to control the emission wavelength of a low noise and low drift cw reference laser 305 to which one comb line of the comb laser 203 is locked. Typically, the various elements will be controlled with different control bandwidths to optimize the overall frequency control. For example, when using an Er fiber comb laser in FIG. 3a, the Er fiber comb laser can be conveniently locked to a commercially available single-frequency Redfern Integrated Optics Inc. (RIO) diode, which can have very small frequency drifts and an optical line width <5 kHz while allowing control of its emission frequency with a bandwidth >1 GHz.

Several alternatives are available for implementing precision spectroscopy systems. A mechanically stable ring down cavity is preferably implemented and for example constructed with low temperature expansion coefficient materials such as metallic Invar or ceramic Zerodur. High reflectivity mirrors are mounted on either side of the ring down cavity, one with a piezoelectric transducer to change the length of the cavity, with the slow corrections from the PDH electronics. As discussed with respect to FIG. 2, the ring down signal is focused onto detector 3, the output of which is sent to either a digitizer or analog system to perform data analysis. The comb laser 203 further provides an absolute measurement of the laser frequency injected into the ring-down cavity by using a separate wavemeter or frequency calibration routines as discussed previously. By using the AOFS for line-narrowing, the cw laser 205 output can be efficiently coupled into the cavity allowing for intra-cavity saturation of many molecular absorption lines. Here the description of the PDH locking scheme is to serve only as an example, modification of the locking scheme can also be implemented.

When line narrowing cw lasers operating in the mid-IR, it is useful to frequency up-convert the cw laser to enable frequency measurements in the near IR (at wavelengths <1.7 μm), where wide bandwidth and high sensitivity photodetectors are readily available. Frequency up-conversion schemes are further useful as they minimize the requirements of the comb laser for line width narrowing.

Figure 4:
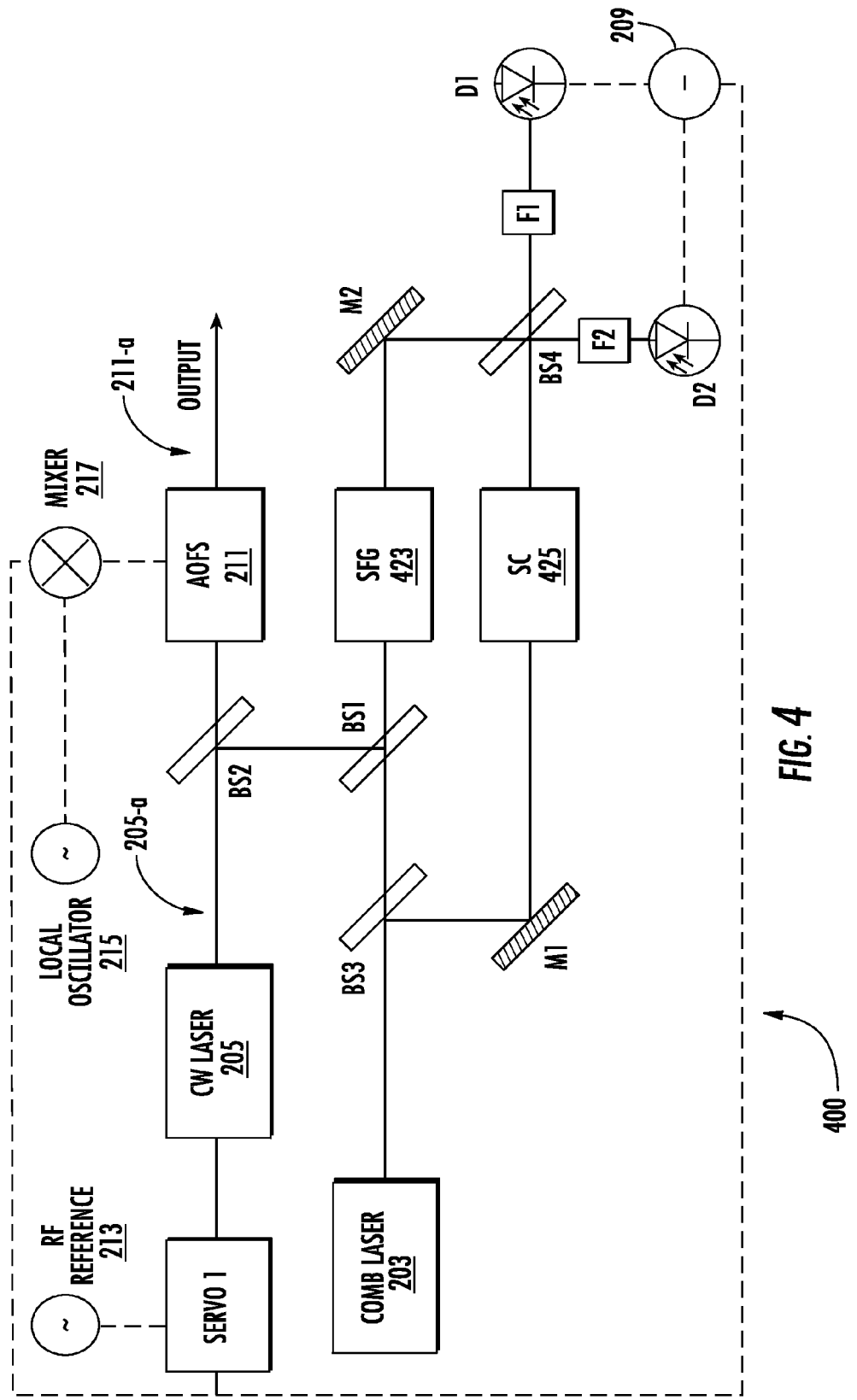
FIG. 4 schematically illustrates an exemplary embodiment for performing frequency measurements and line narrowing in conjunction with frequency up-conversion.

An exemplary scheme 400 for frequency measurements and line narrowing in conjunction with frequency up-conversion is shown in FIG. 4. The arrangement includes several optical and electronic components of the line narrowing system of FIG. 2. However, an additional optical stage 423 designed for sum-frequency generation (SFG) between the cw laser 205 and the frequency comb laser 203 is incorporated. SFG between the cw laser and the frequency comb laser can, for example, be performed by overlapping optical beams from the cw laser 205 and comb laser 203, and focusing the beams into a nonlinear crystal included in optical stage 423. For efficient frequency up-conversion highly nonlinear crystals such as optically patterned GaAs, optically patterned GaP, GaSe or AgGaSe can be implemented. However, a wide selection of nonlinear crystals is available for SFG in the art. Also an additional optical stage 425 for super continuum generation (SC) with the frequency comb laser 203 is included. Beam splitter BS3 is further used to divert part of the light from the frequency comb laser 203 output to the SC generation stage 425. SC generation is typically performed when coupling short, of order <300 fs pulses, into highly nonlinear fibers. In this particular example a high degree of coherence for the generated super continuum is needed, which typically requires pulses with a pulse width <200 fs, as for example described in U.S. patent application Ser. No. 13/415,374, entitled "Broadband generation of mid IR, coherent continua with optical fibers", filed Mar. 8, 2012, which is hereby incorporated by reference in its entirety. SC is well known in the state of the art and not further discussed here. The two light beams from the SC and the SFG stages 425, 423 are optically combined via beam splitter BS4, and optically filtered with identical filters F1 and F2. A beat signal is then detected with detectors D1 and D2. The filters can also be inserted upstream of beamsplitter BS4. Dual balanced detection is further implemented as described with respect to FIG. 2 so as to maximize the S/N ratio of the detected beat signal. Optical hybrids can also be implemented as discussed with respect to FIG. 2.

Figure 5:
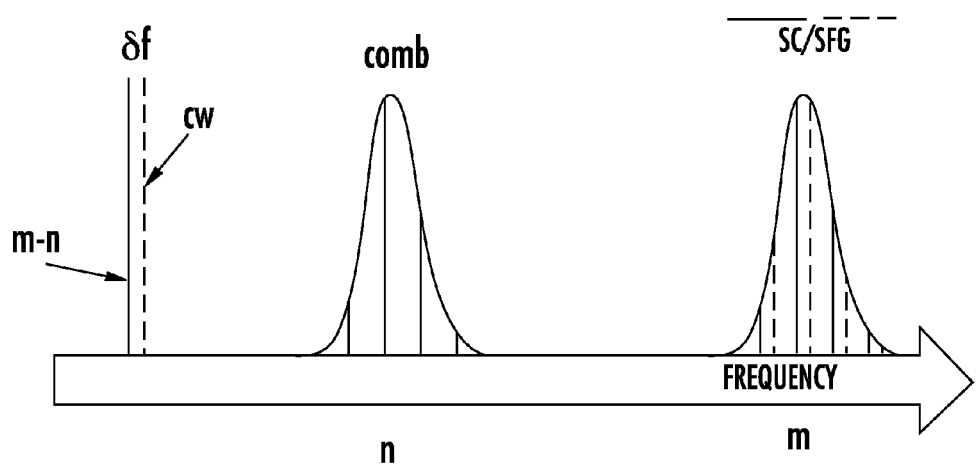
FIG. 5 schematically illustrates the optical frequencies involved in performing frequency measurements and line narrowing in conjunction with frequency up-conversion.

The frequency comb structure generated by the comb source, and the SFG and SC generation process in relation to the cw source are further illustrated with respect to FIG. 5. Here the comb source, say a mode locked oscillator, contains individual frequency lines separated by $\nu_{rep}$, where the center of the frequency lines is assumed to be located near $n \times \nu_{rep}$. The frequency lines are denoted by thin black lines under the spectral envelope corresponding to the comb in FIG. 5. The SC process and the SFG process in turn generate two frequency combs centered near a frequency $m \times \nu_{rep}$; the frequency lines related to SC and SFG are denoted by thin solid and thin dashed lines respectively in FIG. 5. The frequency offset between the SC and SFG lines, $\delta f$, is given by the difference in the frequency of the cw laser and the frequency of the comb line of order m−n. However, the exact value of m−n is initially not known, though it can be determined by using for example a wavemeter or external frequency references.

The frequency of the cw light diffracted by the AOFS, $f_{diff}$, can then be evaluated similarly to the procedure described above in conjunction with eq. (1). As described with respect to FIG. 2, a local oscillator with frequency $f_{LO}$ is used and mixed with a beat frequency $\Delta f_0$ to produce a mean excitation frequency for the AOFS of $\bar{f}_{aofs}$. $\Delta f_0$ is obtained from the beat signal between the SFG comb and the SC comb. $\Delta f_0$ contains the fluctuations of the frequency of the cw laser as shown in FIG. 4. This beat signal can be locked to a certain frequency with a slow servo loop just acting on the cw laser frequency as described with respect to FIG. 2. It can then be shown that the cw light frequency diffracted by the AOFS is given by $$f_{diff} = (m-n) \times f_{rep} + f_{LO}, \tag{2}$$

Similarly to the line narrowing described with respect to FIG. 2, the diffracted cw light is given precisely by the frequency of one comb line plus the local oscillator frequency. In other words the coherence of the comb lines is transferred to the cw laser. In contrast to the line-narrowing scheme from FIG. 2, however, no carrier envelope offset frequency control of the frequency comb laser is required. Hence significant line narrowing can be obtained by precision repetition rate control of the comb laser. For a higher degree of line narrowing one comb tooth of the comb laser can for example be locked to an external reference laser. To obtain a narrow linewidth cw laser output, a narrow line width comb laser is highly desirable. To ensure long term frequency stability of the line-narrowed cw light, stabilization of the repetition rate of the frequency comb laser is required. Line width narrowing of the cw laser to a line width of 10 kHz or less is then possible, which in turn allows efficient coupling of the line narrowed light to a high finesse external enhancement cavity.

In order to determine (m−n) in eq. (2), a wavemeter can be implemented that measures the approximate frequency of the cw laser. To enable the use of low grade wavemeters, high repetition rate lasers, operating at repetition rates >250 MHz are beneficial. Also higher repetition rates produce higher average power for the SFG comb and higher S/N ratios for the required beat frequency measurements.

Equally, the same procedures as discussed with respect to FIG. 2 can be implemented to allow for frequency measurement and frequency tuning of the cw laser. Here a first measurement is performed at a comb repetition rate $f_{rep1}$, providing a beat frequency $\nu_{beat1} = \Delta n \, f_{rep1} - f_{cw}$, where $\Delta n$ is an integer. The repetition rate of the comb laser is then scanned to a value $f_{rep2}$, providing a beat frequency $\nu_{beat2} = (\Delta n + \delta n) f_{rep2} - f_{cw}$. Here $\delta n$ is also an integer and reflects the change in the comb order that is next to $f_{cw}$. The change in $\delta n$ is easily monitored while scanning the repetition rate, thus we have two equations with two unknowns allowing evaluation of the value of $\Delta n$. To increase the certainty for the estimate of $\Delta n$, the same procedure can be repeated for several different repetition rates as explained by Cingöz et al.

In order to perform line narrowing and frequency measurements in the mid-IR spectral region from 3-13 μm, Tm fiber laser combs as described in U.S. patent application Ser. No. 13/026,762, entitled "Compact coherent high brightness light sources for the mid and far IR", filed Feb. 14, 2011, which is hereby incorporated by reference in its entirety, can be implemented. For example cw lasers operating near wavelengths of 3 and 13 μm produce an SFG comb near 1.2 and 1.73 μm respectively, well within the range of coherent super continuum spectra that can be generated with a silica fiber based Tm fiber laser operating near a wavelength of 2 μm in conjunction with a highly nonlinear silica based super continuum fiber.

In various embodiments a limitation of the feedforward schemes as implemented for optical frequency stabilization and line width narrowing arises from inevitable phase delays between the various electronic components as well as non-common mode optical beam paths, particularly in the experimental set-up described with reference to FIG. 4. Therefore systematic phase errors can accumulate in feedforward schemes which limit the accuracy of the achievable line narrowing.

Figure 6:
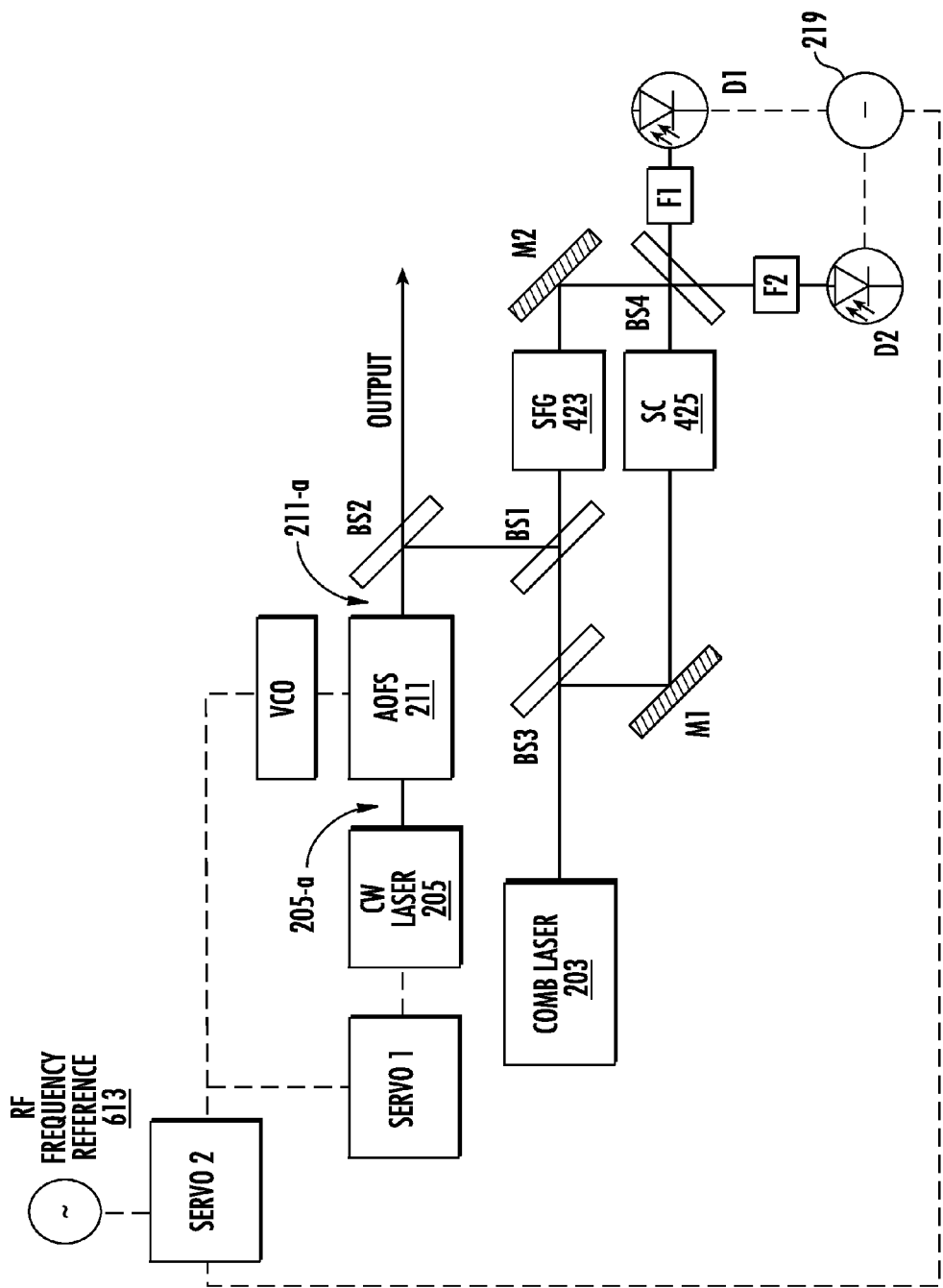
FIG. 6 schematically illustrates an alternative embodiment for performing frequency measurements and line narrowing in conjunction with frequency up-conversion.

One way to avoid such limitations is to incorporate a feedback based optical line narrowing scheme as shown in FIG. 6. In the feedback configuration the detector pair D1, D2 (or optical hybrid as will be shown below) detects the beat frequency between the SFG and the SC comb as described with respect to FIG. 4, where the SFG comb further contains the frequency of the cw laser 205 and is frequency shifted by the modulation frequency $f_{aofs}$ of the AOFS 211. With appropriate feedback control and a narrow-linewidth frequency comb an identical linewidth reduction after the AOFS with respect to the cw-laser is possible. The phase of the beat signal relative to an RF reference signal 613 is stabilized with a phase locked loop, comprising a phase detector and a loop filter in servo 2 (not shown). The loop filter can be implemented as a PID controller. Generally, both a slow and a fast feedback loop are implemented as discussed with respect to FIG. 2. In various embodiments the slow feedback loop is configured as an integrator, with the output (control signal) of the fast feedback loop servo 2 as input. The output from the slow feedback loop servo 1 is then used to coarsely control the wavelength of the cw laser, whereas the fast feedback servo 2 controls the modulation frequency of the AOFS via a voltage controlled oscillator (VCO). The VCO is configured such that at zero input voltage the VCO output frequency is at the center of the acceptance bandwidth of the AOFS. In a practical implementation this can be obtained by a DC offset.

The frequency of the cw light diffracted by the AOFS is then given by $$f_{diff} = (m-n) \times f_{rep} + f_{offset}$$

where the offset frequency is freely selectable by an appropriate control of the VCO frequency. By selecting different values of m−n and $f_{offset}$, the emission frequency from the cw laser can be tuned over large frequency ranges.

The feedback electronics in the present configuration can be designed to be mainly limited by the transit time of the acoustic wave inside the AOFS, as in the feed forward approach discussed with respect to FIG. 2. For a higher bandwidth feedback loop an additional in-line EOM can be implemented as described previously with respect to FIG. 3A. As another alternative, cw lasers with a very high modulation bandwidth can also be implemented. In this case, the AOFS can be eliminated.

The value of m−n can be determined using techniques similar to the ones described with respect to FIGS. 2 and 4. A double pass through the AOFS can further be implemented to avoid any pointing modulations. The line narrowed light can be further coupled into external enhancement cavities as described with respect to FIGS. 3 and 3a for trace gas detection. In contrast to FIG. 3a, the control of the cw laser frequency is interrupted when the AOFS is turned off. This can be overcome by simply frequency detuning the AOFS during the ring down detection stage. For example a voltage step can be applied to the VCO during the ring down detection stage to tune the cw laser emission frequency away from the ring down cavity resonance.

Figure 7:
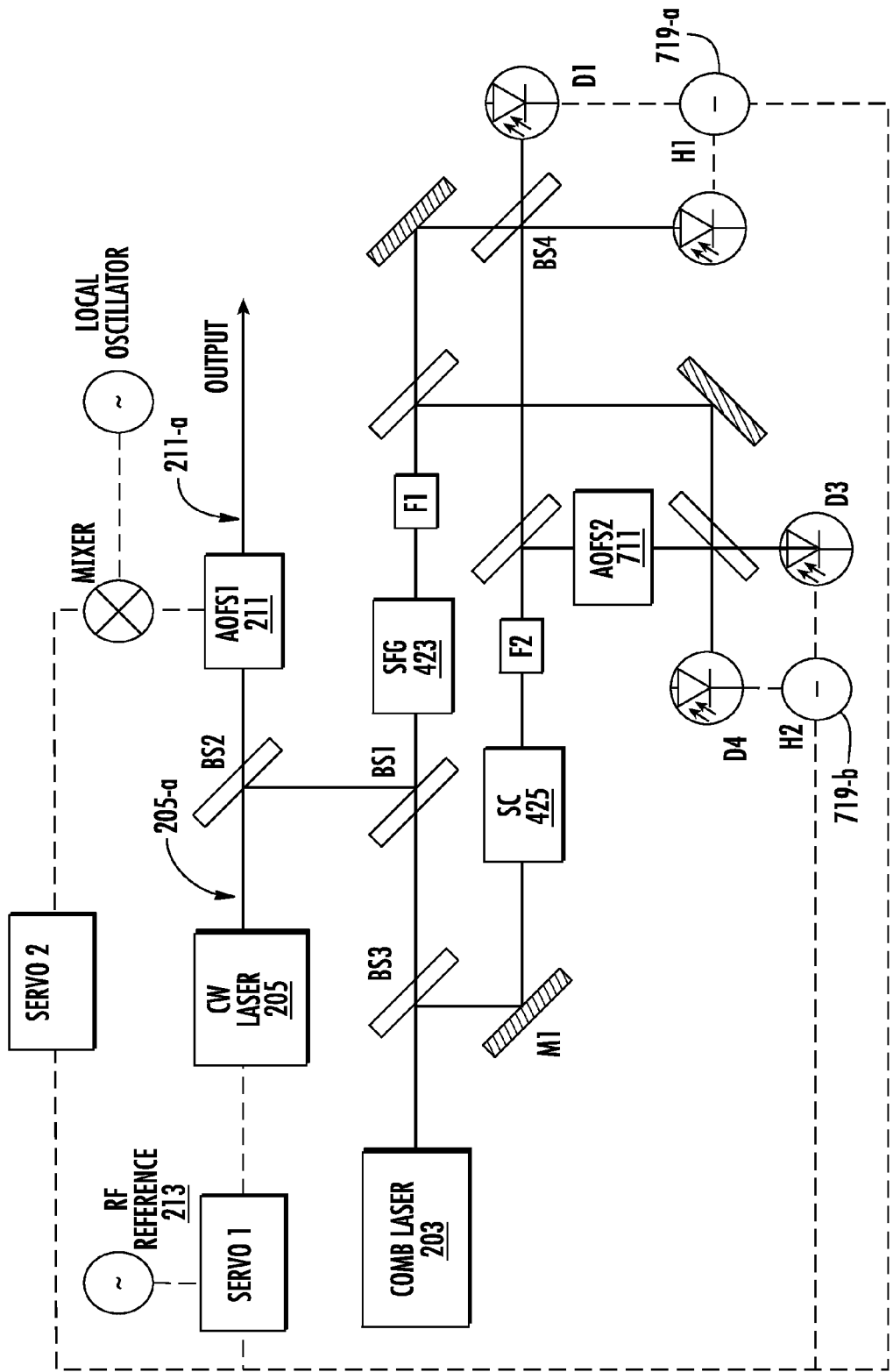
FIG. 7 schematically illustrates an exemplary embodiment of an optical frequency synthesizer in conjunction with frequency up-conversion.

Frequency up-conversion and line narrowing via feedback control with an AOFS can further be combined to construct a widely tunable frequency synthesizer. An implementation for such a synthesizer is shown in FIG. 7. In principle, depending on the possible modulation speed of the cw laser, the first AOFS 211 (AOFS1) is optional. In this example the fast servo loop (servo 2) acts directly on the cw laser and AOFS 1 is omitted. An implementation of an optical frequency synthesizer without AOFS 1 is not separately shown. The operation of the system is very similar to what was already discussed with respect to FIG. 4. Both feed forward and feedback schemes can be implemented for the control of the emission frequency of the cw laser.

The two dual balanced detection pairs are preferably replaced with two optical hybrids 719-a, 719-b, for example, as available from Kylia or other suppliers. The location of the hybrids is here depicted with letters H1 and H2. To construct a widely tunable frequency synthesizer, for example the comb lines of the comb laser can be tuned via changes of the comb laser repetition rate and appropriate control of the AOFS modulation and the local oscillator frequency.

SFG and SC are used to provide a beat signal in the near IR, this is particularly useful for cw lasers operating in the mid-IR, where high bandwidth detectors are not available. This enables implementing a mid-IR frequency synthesizer by only detecting near-infrared signals.

A preferred approach for the construction of a widely tunable frequency synthesizer is related to the work by Schibli et al. To be able to lock the cw laser, or the cw laser and the AOFS1 211, to the comb laser the phase evolution of the beat signal between the SFG comb and the SC comb is detected with optical hybrid H1 and digitized. The digitization is clocked by a reference oscillator. The digital processor is also clocked by a reference oscillator allowing calculation of the phase evolution of a user set RF offset frequency. The phase difference $\Delta\phi$ between the detected and calculated phases is then fed to a software based phase lock, which locks $\Delta\phi$ to zero, as also explained by Schibli et al. Therefore the optical frequency after the AOFS will be exactly offset by a user-set frequency to the frequency difference of two optical comb lines.

By selecting a desired RF reference frequency or reference phase, the beat frequency between the SFG 423 output and the SC comb and therefore the frequency of the cw laser 205 can be tuned to arbitrary values. Moreover, the cw laser 205 can then be swept over the entire comb spectrum. However, difficulties arise near the two degeneracy points in frequency space, i.e. when the beat frequency is zero or corresponds to half the comb spacing. It is therefore beneficial to implement AOFS2 711, which produces a frequency shifted replica of the frequency comb and allows detection of an unambiguous phase difference between the RF reference and the beat signal even at the degeneracy points with hybrid H2. The software is then further configured to continuously switch phase detection between H1 and H2 to allow for continuous frequency tuning of the cw laser.

When using optical hybrids for direct phase detection of beat signals, unambiguous phase information can be obtained even at the two degeneracy points and therefore the second AOFS2 can be omitted. Such an implementation is not separately shown. A limitation with optical hybrids is generally, the need for an optical quarter-wave plate, which limits the possible optical bandwidth of optical hybrids. However, optical hybrids with a bandwidth of 100 nm or more can still be constructed in the mid-IR spectral range. Some cw lasers may further be prone to mode-hops; in this case coarsely measuring the frequency of the cw laser with a wavemeter avoids any ambiguities in frequency selection.

Optical frequency synthesizers are useful to provide well defined optical frequencies for many spectroscopic applications. For example, an optical frequency synthesizer as described here can be directed applied to trace gas detection via photo-acoustic detection. The measurement of certain trace gases then reduces to a measurement of a photo-acoustic response with a frequency set by the frequency synthesizer. Photo-acoustic detection schemes are well known in the state of the art and not further described here.

Thus, the invention has been described in several embodiments. It is to be understood that the embodiments are not mutually exclusive, and elements described in connection with one embodiment may be combined with, or eliminated from, other embodiments in suitable ways to accomplish desired design objectives.

At least one embodiment includes a laser system. The laser system includes a laser source generating a cw output beam at an optical emission frequency, and a frequency comb source to generate a frequency comb. A detection system receives a portion of the cw beam and a portion of the frequency comb. The detection system is configured to generate a beat signal representative of a frequency difference between a line of the frequency comb and the optical emission frequency of the cw output beam. A stabilizer is operatively connected to the detection system to stabilize the beat signal and the cw optical emission frequency. The system further includes a frequency shifter disposed downstream from the laser source, the frequency shifter receiving a portion of the cw output beam as an optical input and a frequency shifted beat signal as an electrical input. The frequency shifter generates a line narrowed and frequency shifted cw laser output, the frequency shifter being driven by a signal derived from the beat signal in a feedforward configuration.

In any or all embodiments the frequency shifted beat signal may be derived by mixing the beat signal with an oscillator signal having a frequency $f_{LO}$, and the optical frequency of the line narrowed and frequency shifted output may be substantially determined by the optical frequency of a comb line and the oscillator frequency, $f_{LO}$.

In any or all embodiments the laser system may include a beam combiner that receives a portion of the frequency comb from the comb source and a portion of the cw output beam, and provides the inputs to the detection system.

In any or all embodiments a beam combiner may be configured to deliver a portion of the cw output beam as the optical input to the frequency shifter.

In any or all embodiments a linewidth of the line narrowed and frequency shifted cw light may be determined by the linewidth of an individual comb line to which the cw laser is locked by the stabilizer and said frequency shifter.

In any or all embodiments a filter may be disposed downstream from the comb laser to limit the number of comb lines and to produce a filtered frequency comb for use with the detection system.

In any or all embodiments a detection system may include a dual balanced detector and electronic filter to isolate a single comb line.

In any or all embodiments the laser system may include a laser cavity disposed downstream from the frequency shifter.

In any or all embodiments a laser cavity may include a ring down cavity, and the ring-down cavity may be operatively connected to the frequency shifter via a feedback loop so as to generate a line narrowed and frequency shifted output while also controlling the light injection and/or light detection periods of the ring-down cavity.

In any or all embodiments the frequency shifter may be configured to generate the line narrowed output and to optically switch the ring down cavity between injection and detection states.

In any or all embodiments a controller may be included to generate control signals so as to control at least the repetition rate of the comb laser and the cavity length of a downstream cavity.

In any or all embodiments the laser system may be arranged as a portion of an optical spectroscopy system.

In any or all embodiments the system the laser system may include a fiber comb laser, and a cw reference laser emitting a reference frequency to which an output of the fiber comb laser is locked, the cw reference laser comprising a single frequency diode laser, wherein the control bandwidth of the controller is sufficiently large to control the emission frequency of the diode laser.

In any or all embodiments the frequency shifter may include an acousto-optic device, an electro-optic device, or a combination thereof.

In any or all embodiments the laser system may further include: a cw reference laser, the cw reference laser and the comb laser arranged such that a comb line is locked to the emission frequency of the cw reference laser.

In any or all embodiments a stabilizer may include a first servo connected to an RF reference source, the servo generating an error signal between the beat signal and an RF reference signal. The stabilizer at least coarsely stabilizes the optical frequency of the laser source based on the error signal.

At least one embodiment includes a laser system. The laser system includes a laser source generating a cw output beam at an optical emission frequency and a frequency comb source to generate a frequency comb. The system further includes frequency up-converter that includes a sum-frequency generation stage (SFG) and a supercontinuum stage (SC) to provide frequency up-conversion, the SFG receiving a portion of the cw beam, the SFG and the SC each receiving a portion of the frequency comb, wherein the SFG and the SC, in combination, generate two frequency combs. A detection system receives a portion of each of the two frequency combs, the detection system being configured to generate a beat signal between the SFG comb and the SC comb. A stabilizer operatively connected to the detection system stabilizes the beat signal and the cw optical emission frequency. A frequency shifter is disposed downstream from the cw laser, the frequency shifter receiving a portion of the cw output beam as an optical input and a frequency shifted version of the beat signal between the SFG comb and the SC comb as an electrical input. The frequency shifter generates a line narrowed and frequency shifted cw laser output.

At least one embodiment includes a laser-based spectroscopy system capable of molecular detection.

For purposes of summarizing the present invention, certain aspects, advantages and novel features of the present invention are described herein. It is to be understood, however, that not necessarily all such advantages may be achieved in accordance with any particular embodiment Thus, the present invention may be embodied or carried out in a manner that achieves one or more advantages without necessarily achieving other advantages as may be taught or suggested herein.

While only certain embodiments have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the embodiments described therein.

What is claimed is:

1. A laser system, comprising:
   a laser source generating a cw output beam at an optical emission frequency;
   a frequency comb source to generate a frequency comb;
   a detection system that receives a portion of said cw beam and a portion of said frequency comb, said detection system configured to generate a beat signal representative of a frequency difference between a line of the frequency comb and the optical emission frequency of the cw output beam;
   a stabilizer operatively connected to said detection system to stabilize said beat signal and said cw optical emission frequency; and a frequency shifter disposed downstream from said laser source, the frequency shifter receiving a portion of said cw output beam as an optical input and a frequency shifted beat signal as an electrical input, wherein said frequency shifter generates a line narrowed and frequency shifted cw laser output, said frequency shifter being driven by a signal derived from said beat signal in a feedforward configuration.

2. The laser system of claim 1, wherein said frequency shifted beat signal is derived by mixing said beat signal with an oscillator signal having a frequency $f_{LO}$, and the optical frequency of the line narrowed and frequency shifted output is substantially determined by the optical frequency of a comb line and the oscillator frequency, $f_{LO}$.

3. The laser system of claim 1, wherein said laser system comprises a ring-down laser cavity disposed downstream from said frequency shifter.

4. The laser system of claim 3, wherein said ring-down cavity is operatively connected to said frequency shifter via a feedback loop so as to generate said line narrowed and frequency shifted output while controlling light injection and/or light detection periods of said ring-down cavity.

5. The laser system of claim 4, wherein said frequency shifter is configured to generate said line narrowed output and to optically switch the ring-down cavity between injection and detection states.

6. The laser system of claim 3, further comprising a controller generating control signals to control at least the repetition rate of said comb laser and the cavity length of said ring-down cavity.

7. The laser system of claim 3, wherein said laser system is arranged as a portion of an optical spectroscopy system.

8. The laser system of claim 1, wherein said laser system comprises a fiber comb laser, and a cw reference laser emitting a reference frequency to which an output of the fiber comb laser is locked, the cw reference laser comprising a single frequency diode laser, wherein the control bandwidth of said controller is sufficiently large to control the emission frequency of said diode.

9. The laser system of claim 1, wherein said frequency shifter comprises an acousto-optic device, an electro-optic device, or a combination thereof.

10. The laser system of claim 1, further comprising: a cw reference laser, said cw reference laser and said comb source are arranged such that a comb line is locked to the emission frequency of said cw reference laser.

11. The laser system of claim 1, wherein said stabilizer comprises a first servo connected to an RF reference source, said servo generating an error signal between said beat signal and an RF reference signal, wherein said stabilizer at least coarsely stabilizes the optical frequency of said laser source based on said error signal.

12. An optical spectroscopy system capable of molecular detection, comprising the laser system of claim 1.

13. A laser system, comprising:
a laser source generating a cw output beam at an optical emission frequency;
a frequency comb source to generate a frequency comb;
a frequency up-converter comprising a sum-frequency generation stage (SFG) and a supercontinuum stage (SC) to provide frequency up-conversion, said SFG receiving a portion of said cw beam, said SFG and said SC each receiving a portion of said frequency comb, wherein said SFG and said SC, in combination, generate two frequency combs;
a detection system that receives a portion of each of said frequency combs, said detection system being configured to generate a beat signal between the SFG comb and the SC comb;
a stabilizer operatively connected to said detection system to stabilize said beat signal and said cw optical emission frequency; and
a frequency shifter disposed downstream from said cw laser, the frequency shifter receiving a portion of said cw output beam as an optical input and a frequency shifted version of said beat signal between the SFG comb and the SC comb as an electrical input,
wherein said frequency shifter generates a line narrowed and frequency shifted cw laser output.

14. An optical spectroscopy system capable of molecular detection, comprising the laser system of claim 13.

* * * * *